United States Patent [19]

Heide et al.

[11] Patent Number: 5,673,685

[45] Date of Patent: Oct. 7, 1997

[54] DEVICE FOR GENERATING INHALABLE ACTIVE SUBSTANCE PARTICLES

[75] Inventors: Helmut Heide, Kelkheim 2; Bernhard Hugemann, Frankfurt/M; Joachim Pabst, Reinheim, all of Germany

[73] Assignee: GGU Gesellschaft Für Gesundheit und Umweltforschung, Frankfurt, Germany

[21] Appl. No.: 344,220

[22] Filed: Nov. 23, 1994

Related U.S. Application Data

[63] Continuation of PCT/EP93/01157, May 11, 1993.

[30] Foreign Application Priority Data

May 29, 1992 [DE] Germany .................. 42 17 787.1

[51] Int. Cl.$^6$ ............................. A61M 15/00
[52] U.S. Cl. ..................... 128/203.15; 128/203.12
[58] Field of Search ................. 128/205.23, 203.12, 128/22.22, 203.14, 203.18, 203.21, 203.23, 203.24, 203.15

[56] References Cited

U.S. PATENT DOCUMENTS

| | | | |
|---|---|---|---|
| 2,587,215 | 2/1952 | Priestly | 128/203.15 |
| 2,622,594 | 12/1952 | Brooks | 128/203.15 |
| 3,027,897 | 4/1962 | Carofiglio | 128/203.15 |
| 3,362,405 | 1/1968 | Hazel | 128/203.15 |
| 3,980,074 | 9/1976 | Watt et al. | 128/203.15 |
| 4,013,075 | 3/1977 | Cocozza | 128/203.15 |
| 4,240,418 | 12/1980 | Rosskamp et al. | 128/203.15 |
| 4,274,403 | 6/1981 | Struve | 128/203.15 |
| 4,524,769 | 6/1985 | Wetterlin | 128/203.15 |
| 4,811,731 | 3/1989 | Newell et al. | 128/203.15 |
| 4,841,964 | 6/1989 | Hurka et al. | 128/203.15 |
| 5,176,132 | 1/1993 | Drought et al. | 128/203.15 |
| 5,201,308 | 4/1993 | Newhouse | 128/203.15 |
| 5,243,970 | 9/1993 | Ambrosio et al. | 128/203.15 |
| 5,301,666 | 4/1994 | Lerk et al. | 128/203.15 |
| 5,331,953 | 7/1994 | Andersson et al. | 128/203.15 |
| 5,341,800 | 8/1994 | Clark et al. | 128/203.15 |
| 5,347,999 | 9/1994 | Poss et al. | 128/203.15 |
| 5,394,868 | 3/1995 | Ambrosio et al. | 128/203.15 |
| 5,429,122 | 7/1995 | Zanen et al. | 128/203.15 |

FOREIGN PATENT DOCUMENTS

| | | |
|---|---|---|
| 0 407 028 | 1/1991 | European Pat. Off. . |
| 40 27 390 | 3/1992 | Germany . |

Primary Examiner—Edgar S. Burr
Assistant Examiner—William J. Deane, Jr.
Attorney, Agent, or Firm—Connolly & Hutz

[57] ABSTRACT

A device for mechanically generating inhalable active substance particles from a consolidated medication supply and for conveying the active substance particles into the respiratory tract, wherein, in order to generate the active substance particles, there is a drivable face mill against which the front of a medication supply in the form of a ring-shaped body can be pressed, whereby the ring-shaped body forms the beginning of an inhalation tube ending in a mouthpiece and in that the housing surrounding the ring-shaped body and the face mill is provided with air inlet openings in the blade area of the face mill and said air inlet openings, together with the depressions located between the blades and the inhalation tube, form an air channel leading to the mouthpiece.

10 Claims, 2 Drawing Sheets

DEVICE FOR GENERATING INHALABLE ACTIVE SUBSTANCE PARTICLES

BACKGROUND OF THE INVENTION

1. Field of the Invention

This application is a continuation of PCT/EP93/01157 filed May 11, 1993 which designated the U.S.

The invention relates to a device for mechanically generating inhalable, active substance particles from a consolidated medication supply and for conveying the active substance particles into the respiratory tract.

2. Description of the Prior Art

European Patent Application No. 0,407,028 A2 describes a device in which a certain dosage of active substance particles is abraded from a consolidated medication supply by means of rotating blades. For this purpose, it is necessary to press the upper part of the device against the blades while rotating it. The active substance particles are conveyed by air suction into the lower part of the device. In this process, two air flows are generated, one through the upper part and one through bypass openings in the lower part.

German Preliminary Published Application No. 40 27 390 discloses a device in which active substance particles are brushed off a consolidated medication supply by means of a rotating brush. The brush is made to rotate by means of a pretensioned friction-gear drive. The brushed-off active substance particles are inhaled by means of an air flow that is sucked in from the bottom through the device.

Both devices have the disadvantage that they are very imprecise in their metering accuracy. Moreover, due to the type of air flow arrangement, an agglomeration of the active substance particles can easily form. In European Patent Application No. 407 028, the abraded active substance particles fall downwards to the bottom of the lower part of the device.

Inhalation is to take place via two air flows. It is evident that such an air flow arrangement can easily get out of control if the flow resistances of the two air paths change due to incorrect operation, for example, if someone inadvertently holds the air inlet openings shut or if the openings become clogged by fragments of the active substance. In German Preliminary Published Application No. 4,027,390, the brushed-off active substance particles have to be sucked in around the brush mechanism and through the brush. As a result, agglomerations are unavoidable.

SUMMARY OF THE INVENTION

The objective of the invention is to create a device which is extremely simple to operate and with which to inhale precisely metered dosages of active substance particles from a consolidated medication supply in a reproducible manner.

The objective of the invention is achieved in that, in order to generate the active substance particles in the device, there is a drivable face mill against which the front of a medication supply in the form of a ring-shaped body can be pressed, whereby the ring-shaped body forms the beginning of an inhalation tube ending in a mouthpiece and in that the housing surrounding the ring-shaped body and the face mill is provided with air inlet openings in the blade area of the face mill and said air inlet openings, together with the depressions located between the blades and the inhalation tube, form an air channel leading to the mouthpiece.

DESCRIPTION OF THE PREFERRED EMBODIMENTS

Figure 1:
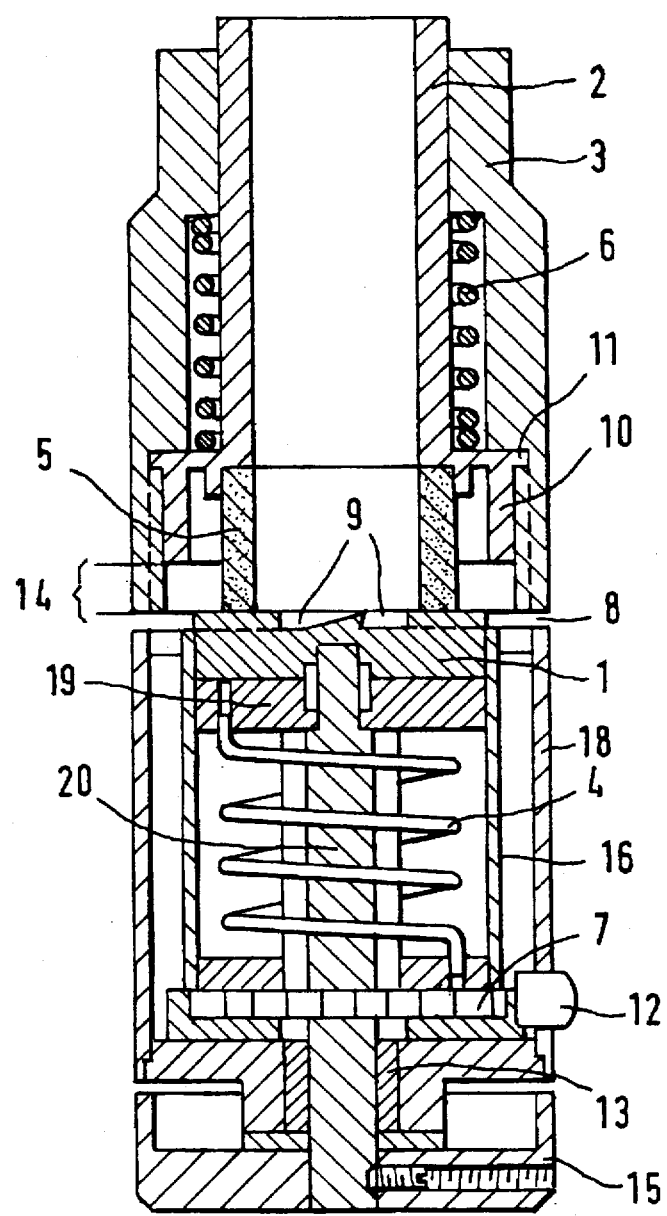
FIG. 1 shows a cross section of the device according to the invention.
Figure 2:
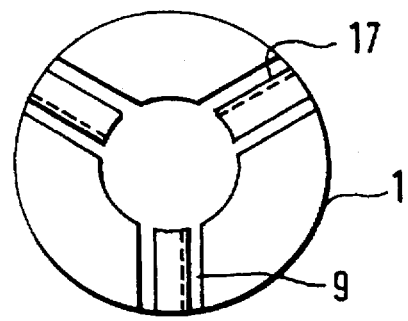
FIG. 2 is a top view of the face mill.
Figure 3:
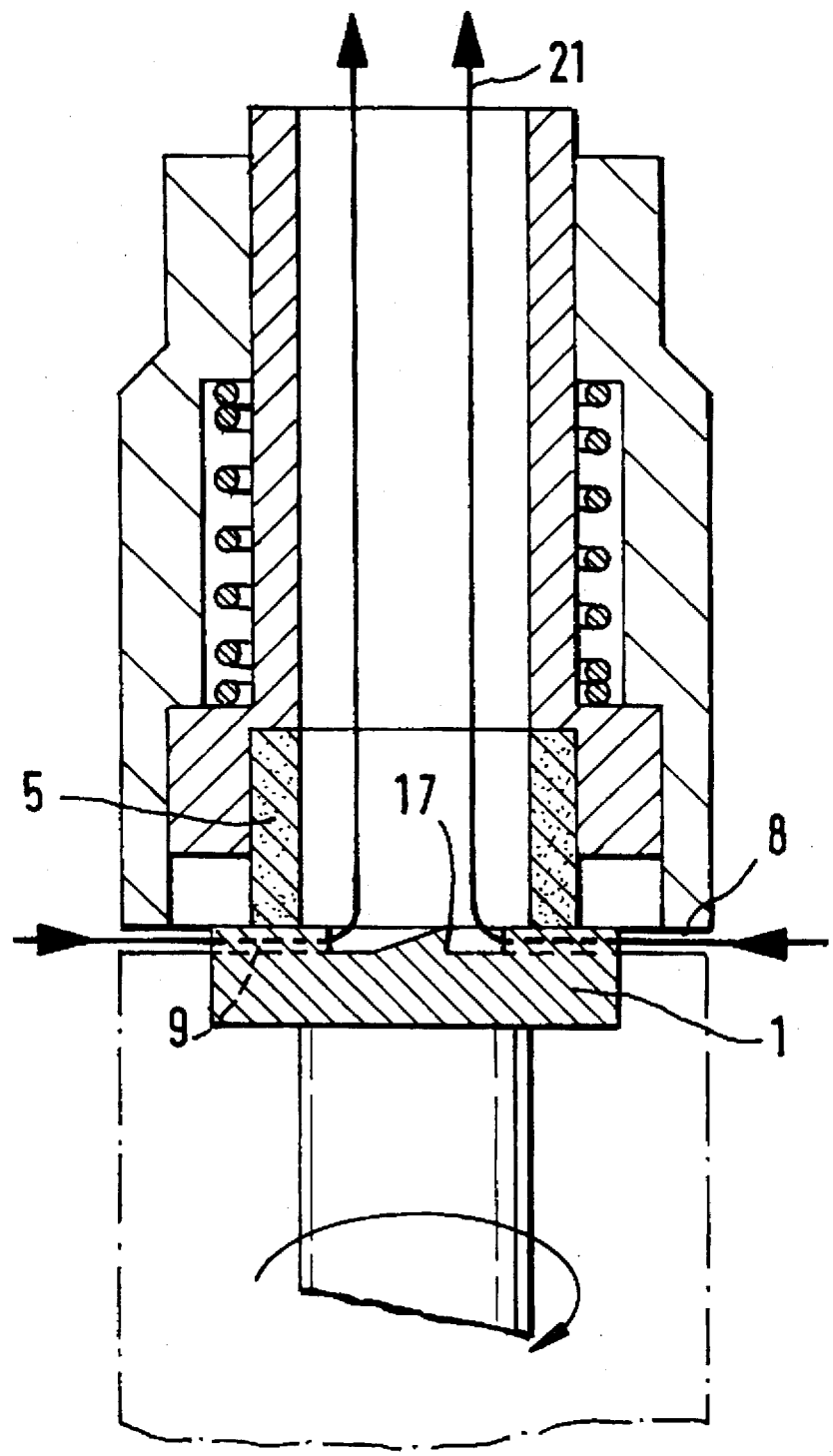
FIG. 3 is the flow path of the air sucked into the device.

The objective the invention is achieved in that, in order to generate the active substance particles in the device, there is a drivable face mill against which the front of a medication supply in the form of a ring-shaped body can be pressed, whereby the ring-shaped body forms the beginning of an inhalation tube ending in a mouthpiece and in that the housing surrounding the ring-shaped body and the face mill is provided with air inlet openings in the blade area of the face mill and said air inlet openings, together with the depressions located between the blades and the inhalation tube, form an air channel leading to the mouthpiece.

In this manner, a flow path is created in which the narrowest point lies between the blades of the face mill, against which the active-substance ting-shaped body is pressed. When an air volume of 1 liter per second is inhaled, flow rates of up to about 200 km per hour are reached. The particles generated by the face mill are carded off at the point in time when they are formed and cannot agglomerate with the particles that follow. Moreover, due to this jet effect, a marked distribution of the particle concentration in the air flow is achieved. The metered dosage is determined by the number of revolutions of the face mill. The size of the particles is essentially determined by the geometry of the face mill, by the compactness of the active-substance ring-shaped body and by the contact pressure of the ring-shaped body against the face mill as well as by the velocity of the air at the blades.

The active substance body protrudes out of the inhalation tube. The inhalation tube has a stroke-limiting stop so that the active substance body can be replaced in time before being used up completely.

The ring-shaped body is arranged together with the inhalation tube so as to be replaceable. All that is necessary for this purpose is to take off the upper part of the device.

A very important aspect of the invention is the geometrical design of the active substance body. Its ring-shaped design has the following advantages: the inner hollow space of the ring-shaped body is part of the inhalation tube through which the active substance particles flow together with the inhalation air immediately after being generated. In this manner, dead flow zones and thus deposits of particles are avoided. With a ring, the wall thickness can be selected in such a way that the differences in cutting speeds of the face mill on the inner and outer ting diameter are negligible with respect to the total surface. It is known that the cutting speed in the center of a solid body would be zero. This would lead to an undefinable abrasion of the active substance body and thus to an undefined particle generation.

The device can be used in medical applications for different types of active substance bodies. In order to avoid confusion, the inhalation tube has a coded identification that matches one specific type of drug.

The device can also be used for inhaling through the nose.

The face mill is rotated by a spring-loaded drive whereby the number of revolutions can be set ahead of time. The use of battery-powered, miniature gear electric motors is also possible.

Independent of this, the particle generation time is much shorter than the total inhalation time. In general, it is only mounts to fractions of a second. Consequently, this invention means that the coordination of the particle generation and of the inhalation procedure is not a problem for the patients.

FIG. 1 shows the face mill 1 which is attached to a shaft 20. On the shaft 20, there is also a notched wheel 7 and, at the lower end, a return stop 13. In the area of the spring motor housing 16, there is a drive spring 4 which concentrically surrounds the shaft 20. The drive spring 4 is attached, on the one hand, in the upper part 19 of the spring motor housing 16 and, on the other hand, in the notched wheel 7. By turning the wind-up button 15, the spring 4 is tensioned. By pressing the activation mechanism 12, the face mill 1 is made to rotate.

The upper part of the device has the inhalation tube 2 at whose lower end the medication supply 5 in the form of a consolidated active-substance ring-shaped body is inserted. The inhalation tube i is pressed together with the medication supply 5 by means of the contact spring 6 against the face mill 1. As a result, the from of the medication supply 5 is always in contact with the face mill 1. At the lower end of the inhalation tube 1, there is a protuberance 10 that serves as a consumption limiter. Once it comes into contact with the inhalator housing, no more particles can be generated. The consumption range is shown by the two arrows 14. Moreover, as identification of the active substance and the parameters set for it in the device, there are two bolts 11 here which function as a key plug in conjunction with the mouthpiece 3.

The upper and the lower part of the device are connected by means of guide pins not shown here. Between the upper and lower part, there is an annular gap 8 which serves as an air inlet. As can be seen in FIG. 1, this air inlet is positioned in the area of the blades 17 of the face mill 1.

FIG. 2 shows a top view of the blades 17 and the depressions 9 in from of and behind the blades 17.

FIG. 3 shows the flow path of the sucked-in air and the active substance particles. The air passes through the tingshaped air inlet 8 and recedes into the depressions 9 in front of and behind the blades 17 of the face mill 1 and from there directly into the central channel formed by the active-substance ring-shaped body 5 and of the inhalation tube 2 to the mouth of the patient and into the respiratory tract. Since there is only a very small cross section in the flow path in the area of the front of the active-substance ring-shaped body 5 and the face mill 1, even if the patient generates only a very small suction volume, the air speed is still adequate for the inhalation of the generated active substance particles.

The device is operated in the following manner: the drive spring 4 is tensioned by means of the wind-up button 15. At the same time as the inhalation, pressing the activation mechanism 12 unlocks the drive spring 4, thereby making the face mill 1 rotate. The rotation phase lasts only fractions era second.

I claim:

1. Device for mechanically generating inhalable active substance, particles by abrading a ring-shaped and consolidated medication supply by means of a rotating metering means and an air channel which leads from the area of the metering means to the mouthpiece, wherein the ring-shaped medication supply itself and parts of the metering means form the air passage to the mouthpiece and the air inlet openings in the housing are located in the area of the metering means.

2. The device according to claim 1, wherein a drivable face mill serves as the metering means, against which the front of the ring-shaped medication supply can be pressed.

3. The device according to claim 2, wherein the air inlet openings are located in the housing in the area of the blades of the face mill.

4. The device according to claim 3, wherein the inhalation tube with the ring-shaped body is pressed at a defined pressure by means of a contact spring against the face mill.

5. The device according to claim 4, wherein the stroke path of the inhalation tube with the medication supply can be limited.

6. The device according to claim 4, wherein the ring-shaped body is arranged together with the inhalation tube in such a way that they can be replaced.

7. The device according to claim 2, wherein the inhalation tube has a coded identification that matches one specific type of drug.

8. The device according to claim 2, wherein the face mill is rotated by a spring-loaded drive.

9. The device according to claim 8, wherein the number of revolutions of the face mill can be set in advance.

10. The device according to claim 8, wherein the depressions in front of and behind the blades of the face mill (1) have the smallest cross section of the entire flow path.

* * * * *